United States Patent
Mangold et al.

(10) Patent No.: US 7,482,132 B2
(45) Date of Patent: Jan. 27, 2009

(54) METHOD FOR DETERMINING THE ACTIVITY OF ORNITHINE DECARBOXYLASE AND FOR IDENTIFYING EFFECTORS OF ORNITHINE DECARBOXYLASE ACTIVITY

(75) Inventors: Ursula Mangold, Allston, MA (US); Ekkehard Leberer, Germering (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 637 days.

(21) Appl. No.: 10/318,794

(22) Filed: Dec. 13, 2002

(65) Prior Publication Data

US 2003/0165811 A1 Sep. 4, 2003

Related U.S. Application Data

(60) Provisional application No. 60/356,803, filed on Feb. 13, 2002.

(30) Foreign Application Priority Data

Dec. 13, 2001 (DE) ................ 101 61 412

(51) Int. Cl.
*C12Q 1/48* (2006.01)
*G01N 33/573* (2006.01)
(52) U.S. Cl. ......................... 435/15; 435/7.4
(58) Field of Classification Search ............. 435/4, 435/183, 184, 232, 243, 68.1, 7.4, 15, 255.1, 435/483, 69.1, 471
See application file for complete search history.

(56) References Cited

U.S. PATENT DOCUMENTS 7,063,854 B1 * 6/2006 Gaiger et al. ............ 424/277.1

FOREIGN PATENT DOCUMENTS

WO    WO 99/24571    5/1999
WO    WO 02/077245   10/2002

OTHER PUBLICATIONS

Glikman et al. "Polyamine invilvement in basal and estradiol-stimulated insulin-like growth factor I secretion and action in breast cancer cells in culture" J. Steroid Biochem. Molec. Biol. (1990) 37(1): 1-10.*
Invitrogen Website (www.invitrogen.com/content) accessed on Apr. 3, 2006 (2 page printout).*
Illingworth et al. "Interactions of the human, plant and yeast ornithin decarboxylase subunits and human antizyme" Biochem. Soc. Trans. (1998) 26: 601-606.*
Ramamoorthy et al. "Estrogenic activity of a dieldrin/toxaphene mixture in the mouse uterus, MCF-7 human breast cancer cells, and yeast-based estrogen receptor assays: No apparent synergism" Ecdocrinology (1997) 138: 1520-1527.*
Klein et al. "Recombinant microorganisms . . . " J. Biomolec. Screening (1997) 2: 41-49.*
Hsieh et al. "Expression of human chromosome . . . " Cancer Res. (1990) 50: 2239-2244.*
Moshier et al. "Isolation and expression . . . " J. Biol. chem. (1990) 265(9): 4884-4892.*
Koguchi et al. "Cloning and sequencing . . . " Biochim. Biophys. Acta (1997) 1353: 209-216.*
Hayashi et al. "Characterization of the human antizyme gene" Gene (1997) 203: 131-139.*
Koguchi K. et al., Control Of Ornithine Decarboxylase Activity By Polyamines And Absence Of Antizyme In Tetrahymena, Comp. Biochem. Physiol., (1996), vol. 113B, No. 1, pp. 157-162.
Murakami Yasuko et al., Cloning Of Antizyme Inhibitor, A Highly Homologous Protein To Ornithine Decarboxylase, The Journal Of Biological Chemistry, (1996), vol. 271, No. 7, pp. 3340-3342.
Murakami Yasuko et al., Properties And Fluctuations In Vivo Of Rat Liver Antizyme Inhibitor, Biochem J., (1989), vol. 259, pp. 839-845.
Onoue Hisashi et al., Changes In Ornithine Decarboxylase And Antizyme Activities In Developing Mouse Brain, Biochem J., (1988), vol. 250, pp. 797-803.
Yuan Qing et al., Polyamine Regulation Of Ornithine Decarboxylase And Its Antizyme In Intestinal Epithelial Cells, Am. Journal Physiol Gastrointest Liver Physiol, (2001), vol. 280, pp. G130-G138.
Catherine S. Coleman et al., Assay of Mammalian Ornithine Decarboxylase Activity Using [14C] Ornithine, Methods in Molecular Biology, vol. 79, pp. 41-44.
David J. Feith et al., Targeted Antizyme Expression in the Skin of Transgenic Mice Reduces Tumor Promoter Induction of Ornithine Decarboxylase and Decreases Sensitivity to Chemical Carcinogenesis, Cancer Research, vol. 61, pp. 6073-6081, 2001.
Dominik Mumberg et al., Regulatable Promoters of *Saccharomyces cerevisiae* Comparison of Transcriptional Activity and Their Use for Heterologous Expression, Nucleic Acid Research, vol. 22, No. 25, pp. 5767-5768, 1994.
Dominik Mumberg et al., Yeast Vectors for the Controlled Expression of Heterologous Proteins in Different Genetic Backgrounds, Gene, vol. 156, 1995, pp. 119-122.
J. Janne et al., On the Purification of L-Ornithine Decarboxylase From Rat Prostate and Effects of Thiol Compounds on the Enzyme, Journ. of Bio. Chem., vol. 246, No. 6, pp. 1725-1732, 1971.
Manabu Kawada et al., The Long-Lasting Antiproliferative Effect of 15-Deoxyspergualin Through its Spermidine Moiety, The Journal of Antibiotics, vol. 53, No. 7, pp. 705-710, 2000.
Manas K. Chattopadhyay et al., Antizyme Regulates the Degraduation of Ornithine Decarboxylase in Fission Yeast Schizosaccharomyces Pombe, Journ. of Bio. Chem., vol. 276, No. 26, pp. 21235-21241, 2001.
N. Seiler et al., The Natural Polyamines and the Immune System, Progress in Drug Research, vol. 43, pp. 87-141, 1994.

(Continued)

*Primary Examiner*—Irene Marx
*Assistant Examiner*—Susan Hanley

(57) ABSTRACT

The present invention relates to a method for determining the activity of ornithine decarboxylase and for identifying effectors of ornithine decarboxylase activity, to the effectors of ornithine decarboxylase activity, and to the use thereof as pharmaceuticals for the treatment of disorders of the polyamine level.

6 Claims, No Drawings

OTHER PUBLICATIONS

N. Seller, Oxidation of Polyamines and Brain Injury, Neurochemical Research, vol. 25, No. 4, 2000.

R. Daniel Gietz et al., Studies on the Transformation of Intact Yeast Cells by LiAc/SS-DNA/PEG Procedure, Yeast, vol. 11, pp. 355-360, 1995.

R.D. Klein et al., Haemonchus Contortus; Cloning and Functional Expression of a cDNA Encoding Ornithine Decarboxylase and Development of a Screen for Inhibitors, Environmental Parasitology, vol. 87, pp. 171-184, 1997.

Randall K. Saiki et al., Enzymatic Amplification of Beta Globin Genomic Sequences and Restriction Site Analysis for Diagnosis of Sickle Cell Anemia, Science, vol. 230, pp. 1350-1354, (1985).

Satoshi Iwata et al., Anti-Tumor Activity of Antizyme Which Targets the Ornithine Decarboxylase (ODC) Required for Cell Growth and Transformation, Oncogene, vol. 18, pp. 165-172, 1999.

T. David Johnson, Polyamines and Cerebral Ischemia, Progress in Drug Research, vol. 50, pp. 192-229, 1998.

* cited by examiner

METHOD FOR DETERMINING THE ACTIVITY OF ORNITHINE DECARBOXYLASE AND FOR IDENTIFYING EFFECTORS OF ORNITHINE DECARBOXYLASE ACTIVITY

The present invention relates to a method for determining the activity of ornithine decarboxylase and for identifying effectors of ornithine decarboxylase activity.

Ornithine decarboxylase (L-ornithine carboxy-lyase, ODC, IUBMB nomenclature classification: EC 4.1.1.17) is a key enzyme in polyamine biosynthesis. Polyamines play an essential part in cell growth, cell differentiation and protein biosynthesis. Polyamine biosynthesis and the transport of polyamines are regulated in diverse ways at different levels. ODC also assumes an important role in tumorigenesis, since tumor cells have an increased ODC activity. Thus, for example, overexpression of ODC leads to neoplastic transformation (Auvinen et al.). The yeast gene which is homologous to the human ODC gene is called SPE1 (ORF YKL184w). The assay methods for determining ODC activity have normally been effected using radiolabeled substrates such as, for example, [$^{14}$C]ornithine (Coleman & Pegg, 1998, Janne & Williams-Ashman, 1971).

At the protein level, ODC activity and stability are regulated by antizymes (AZ). Antizymes are proteins which bind to ODC, inhibit the enzymatic activity of ODC and stimulate the proteolytic degradation of ODC (Hayashi et al., (1996) TIBS 21, 27-30). In addition, antizymes also regulate polyamine transport into the cell. There are moreover references in the literature to antitumor activity of antizymes (Feith et al., 2001).

In humans, at present four (non-allelic) members of the antizyme family are known, in some cases with very little homology, antizyme 1 (e.g. Acc. No. D87914), antizyme 2 (e.g. Acc. No. AF057297), antizyme 3 (e.g. Acc. No. AF175296), and antizyme 4 (e.g. Acc. No. AF293339).

Whereas baker's yeast (*Saccharomyces cerevisiae*) contains no antizyme homolog (Zhu et al., Bioinformatics, Vol.16, 478-481), the fission yeast Schizosaccharomyces pombe has an antizyme-like protein (Chattopadhyay et al., 2001).

An antizyme inhibitor (AZI) has been described as an antizyme regulatory element and binds with high affinity to antizyme and is even able to release ODC bound in the ODC-AZ complex. There is increased expression of AZI in gastric cancer (Jung et al., (2000), Genomics 69, 281-286).

There is great interest in more detailed investigation of the regulation of ODC activity in order to identify, in the context of tumorigenesis and metastasis, effective substances which influence ODC activity (ODC effectors), i.e. are able to have an influence on ODC activity directly or indirectly (Regulation of ODC activity), for suppression of these processes.

Klein et al. (1997) describe the cloning and functional heterologous expression of an ODC cDNA from the nematode H. contortus in *E.coli* and in *S. cerevisiae* and the use of the transgenic yeast (ΔSPE1) for identifying ODC inhibitors with antiparasitic activity. However, the assay system described by Klein et al. uses spermidine to abolish polyamine depletion and takes no account of the complex regulation of ODC under physiological conditions in mammals, so that it was an object of the present invention to provide a convenient method which can be used to identify active substances which modulate ODC activity, in particular in the context of the activity of AZ and AZI.

As described in detail hereinafter, the object stated above is achieved according to the invention by the embodiments described in the claims. It has been found, surprisingly, that the expression of ODC and AZ and, where appropriate, of AZI in a suitable cellular system—as described hereinafter—leads to achievement of the stated object.

The assay methods of the invention allow specific identification of effectors of ODC activity, especially taking account of the balance between ODC, AZ and, where appropriate, AZI. The use according to the invention of putrescine for abolishing polyamine depletion and the inhibition of cell growth associated therewith makes specific identification of effectors of ODC activity possible, because the inhibition of other enzymes such as, for example, of S-adenosylmethionine decarboxylase on use of spermidine is avoided. It is therefore also possible by use of the methods of the invention to investigate satisfactorily the activity and regulation of the activity of AZ and AZI. It is moreover possible by means of the methods of the invention to identify effectors of AZ and of AZI. The methods of the invention additionally have the advantage that they are suitable for determining ODC activity and identifying effectors of ODC, of AZ and of AZI in a high-throughput screening (HTS).

The present invention therefore relates to a method for determining the activity of ornithine decarboxylase (ODC), in which cells which express ODC and, where appropriate, antizyme and/or antizyme inhibitor are cultivated on a polyamine-free medium in the presence and absence of putrescine, and the growth of said cells is determined.

The present invention also relates to a method for determining the activity of antizyme, in which cells express ornithine decarboxylase (ODC) and antizyme and, where appropriate, antizyme inhibitor are cultivated on a polyamine-free medium in the presence and absence of putrescine and the growth of said cells is determined.

The present invention additionally relates to a method for determining antizyme inhibitor activity, in which cells which express ornithine decarboxylase (ODC), antizyme and antizyme inhibitor are cultivated on a polyamine-free medium in the presence and absence of putrescine, and the growth of said cells is determined.

The present invention further relates to a method for identifying effectors of ornithine decarboxylase (ODC), in which cells which express ODC and, where appropriate, antizyme and/or antizyme inhibitor are cultivated in the presence of a test substance to be investigated on a polyamine-free medium in the presence and absence of putrescine, and the growth of said cells is determined.

The present invention also relates to a method for identifying effectors of antizyme (AZ), in which cells which express ornithine decarboxylase (ODC) and antizyme and, where appropriate, antizyme inhibitor are cultivated in the presence of a test substance to be investigated on a polyamine-free medium in the presence and absence of putrescine, and the growth of said cells is determined.

The present invention further relates to a method for identifying effectors of antizyme inhibitor (AZI), in which cells which express ornithine decarboxylase (ODC), antizyme and antizyme inhibitor are cultivated in the presence of a test substance to be investigated on a polyamine-free medium in the presence and absence of putrescine, and the growth of said cells is determined.

The invention also relates to effectors of ornithine decarboxylase (ODC), of antizyme (AZ) and of antizyme inhibitor (AZI) which have been identified by one of the methods of the invention.

The effectors identified according to the invention bring about, via modulation of the activity of ornithine decarboxylase (ODC), a change in the polyamine concentration and are therefore valuable agents for the therapy and prophylaxis of diseases associated with a polyamine level which is too low or high or are caused thereby, or for whose therapy or propylaxis an increase or reduction in the polyamine level present is desired. Activation or inhibition of ODC activity by the effectors identified according to the invention can be investigated for example in the method of the invention.

Diseases and pathological states associated with a polyamine level which is too low or too high or in which an increase or reduction in the polyamine level is desired and for whose therapy and prophylaxis the effectors of the invention can be employed are present for example in tumorigenesis, in metastatic processes, in disorders of the central nervous system (Johnson 1998, Seiler 2000) or of the immune system (Seiler & Atanassov, 1994, Kawada et al., 2000). ODC inhibitors such as DFMO (Eflornithine, Aventis) are already employed in the therapy of sleeping sickness.

The effectors of the invention can thus be used on animals, preferably on mammals, and in particular on humans, as pharmaceuticals on their own or in the form of pharmaceutical preparations. The present invention therefore also relates to the effectors of the invention for use as pharmaceuticals, to their use for normalizing a disturbed polyamine balance and, particularly, to their use in the therapy and prophylaxis of the abovementioned pathological states, and to their use for the production of medicaments therefor. The present invention further relates to pharmaceutical products which comprise as active ingredient an effective dose of at least one effector of the invention in addition to conventional pharmaceutically acceptable carriers and additives.

The pharmaceuticals can be administered orally, for example in the form of pills, tablets, film-coated tablets, sugar-coated tablets, granules, hard and soft gelatin capsules, aqueous, alcoholic or oily solutions, syrups, emulsions or suspensions, or rectally, for example in the form of suppositories. The administration can, however, also take place parenterally, for example subcutaneously, intramuscularly or intravenously in the form of solutions for injection or solutions for infusion. Further suitable administration forms are, for example, percutaneous or topical administration, for example in the form of ointments, tinctures, sprays or transdermal therapeutic systems, or administration by inhalation of solutions or dry powders in the form of pulmonary sprays, nasal sprays or aerosols, or for example microcapsules, implants or rods. The preferred administration form depends, for example, on the disease to be treated and its severity.

The invention further relates to a method for producing a pharmaceutical comprising at least one of the effectors of the invention and pharmaceutically acceptable carriers and excipients, in which said effector and the pharmaceutically acceptable carriers and excipients are formulated to a pharmaceutical.

The invention further relates to a method for producing a pharmaceutical, comprising
 a) identification of an effector of ornithine decarboxylase (ODC), of antizyme (AZ) or of antizyme inhibitor (AZI) by means of one of the methods of the invention;
 b) provision or preparation of said effector; and
 c) formulation of said effector using pharmaceutically acceptable carriers and/or excipients.

And the invention further relates to a pharmaceutical composition comprising one or more of the effectors of the invention and pharmaceutically acceptable carriers and/or excipients.

The pharmaceutical products of the invention can be produced in a manner known per se. This is done by converting one or more effectors of the invention together with one or more solid or liquid pharmaceutical carriers and/or excipients and, if desired, in combination with other active pharmaceutical ingredients with a therapeutic or prophylactic effect into a suitable administration form or dosage form, which can then be used as pharmaceutical in human medicine or veterinary medicine.

For producing, for example, pills, tablets, sugar-coated tablets and hard gelatin capsules it is possible to use lactose, starch, for example corn starch, or starch derivatives, talc, stearic acid or salts thereof etc. Carriers for soft gelatin capsules and suppositories are, for example, fats, waxes, semisolid and liquid polyols, natural or hardened oils etc. Examples of carriers suitable for producing solutions, for example solutions for injection, or emulsions or syrups are water, physiological saline, alcohols such as ethanol, glycerol, polyols, sucrose, invert sugar, glucose, mannitol, vegetable oils etc. The effectors of the invention can also be lyophilized, and the resulting lyophilizates can be used for example for producing products for injection or infusion or powders for inhalation. Examples of suitable carriers for microcapsules, implants or rods are copolymers of glycolic acid and lactic acid.

The pharmaceutical products may, besides the active ingredients and carriers, also contain conventional excipients or additives, for example fillers, disintegrants, binders, lubricants, wetting agents, stabilizers, emulsifiers, dispersants, preservatives, sweeteners, colorants, flavorings or aromatizing agents, thickeners, diluents, buffer substances, also solvents or solubilizers or means for achieving a depot effect, salts to alter the osmotic pressure, coating agents or antioxidants.

The dosage of the effector of the invention to be administered depends on the individual case and must be adapted as usual to the individual circumstances for an optimal effect. Thus, it depends on the nature and severity of the disease to be treated and on the sex, age, weight and individual response of the person or animal to be treated, on the strength of action and duration of action of the compounds employed, whether therapy is acute or chronic or prophylaxis is applied, or on whether other active ingredients are administered in addition to the effectors of the invention.

The effectors of the invention modulate ODC activity. Because of this property they can be employed not only as active pharmaceutical ingredients in human medicine and veterinary medicine but also as a scientific tool or as an aid for biochemical investigations in which it is intended to influence ornithine decarboxylase activity, and for diagnostic purposes, for example for in vitro diagnosis of cell or tissue samples.

The invention further relates to a test kit for carrying out a method of the invention for determining the activity of ornithine decarboxylase (ODC) or for determining effectors of the activity of ODC, of AZ or of AZI, comprising cells which express ODC and, where appropriate, antizyme and/or antizyme inhibitor.

The term "ornithine decarboxylase (ODC)" encompasses for the purposes of the present invention enzymes which are to be included in the class EC 4.1.1.17 according to the international enzyme classification, for example human (Acc. No. X16277 for the genomic sequence, M31061 for the cDNA), rat (Acc. No. J04792), mouse (Acc. No. X07392), *C. elegans* (Acc. No. U03059), preferably ODC from vertebrates, particularly preferably from mammals, especially of human origin. "Activity of ornithine decarboxylase" means for the purposes of the present invention enzymatic activity according to EC 4.1.1.17 which shows a protein. "ODC activity" can be measured quantitatively or qualitatively in a cellular system, e.g. by measuring the growth of the cells on polyamine-free medium in the presence and absence of putrescine, which can be enhanced for example by color reactions. In a particular embodiment of the method of the invention, cell growth is detected through a reporter gene (e.g. lacZ, GFP) which is under the control of a constitutive promoter. The term "antizyme" means for the purposes of the present invention antizymes of ODC of any origin, i.e. proteins which bind to ODC and inhibit the enzymatic activity of ODC, for example Acc. No. D87914, AF057297, AF175296 or AF293339 for human AZ. "Antizyme activity" means for the purposes of the present invention the ability of an antizyme molecule to inhibit ODC activity. The term "antizymes" also encompasses for the purposes of the invention, fragments, mutants, allelic or splice variants of antizymes having antizyme activity. The term "antizyme inhibitor" means for the purposes of the present invention the inhibitor of ODC antizyme, for example Acc. No. D88674 (human), AF032128 (mouse), D89983 (rat). "Activity of antizyme inhibitor" means for the purposes of the present invention the ability of an antizyme inhibitor molecule to inhibit the activity of an AZ molecule. The term "antizyme inhibitor" also encompasses for the purposes of the invention fragments, mutants, allelic or splice variants of antizymes having antizyme inhibitor activity.

The term "polyamine-free medium" means, for the purposes of the present invention, solid, semisolid or liquid cell culture media otherwise suitable for cultivating the cells employed according to the invention, but comprising insuficient polyamines to support substantial growth of polyamine-dependent cell strains. Preferably, the polyamine-free medium of the invention contains no polyamines. Examples of polyamines include, but are not limited to, putrescine, spermidine and spermine. The term "in the presence of putrescine" means for the purposes of the present invention a putrescine concentration of from 0.1 to 1000 µM, preferably 2 to 500 µM, in particular from 5 to 50 µM, in the cell culture media.

"Cells which express ornithine decarboxylase (ODC)" means for the purposes of the present invention in principle every prokaryotic or eukaryotic cell, e.g. from bacteria, yeasts, algae, plants, nematodes, mammals, or else cells of human origin, in particular cells from yeasts, C. elegans, CHO or HEK cells, which express a functional homologous and/or heterologous ODC, preferably yeast and bacterial cells, in particular yeast cells.

For the purposes of the invention, expression of ODC in a cell can be achieved either by the cell comprising an endogenous/homologous nucleic acid which encodes a protein which has the activity of a homologous ODC, or by the cell being transfected with an exogenous/heterologous nucleic acid by known methods in order to encode a heterologous protein which has the activity of an ODC. It is possible where appropriate for said heterologous protein to be expressed in a cell whose endogenous ODC expression has been inhibited or suppressed in a suitable way, e.g. by known methods of molecular biology, such as, for example, through deletion of the endogenous ODC gene ("knock-out"), by antisense or cosuppression. Expression of an antizyme (AZ) in a cell can be achieved according to the invention either by the cell comprising endogenously a homologous nucleic acid which encodes a protein which has the activity of an AZ, or by the cell being transfected with a heterologous nucleic acid by known methods in order to encode a heterologous protein which has the activity of an AZ. It is possible where appropriate for said heterologous protein to be expressed in a cell whose endogenous AZ expression has been inhibited or suppressed in a suitable way, e.g. through deletion of the endogenous AZ gene ("knock-out"), by antisense or cosuppression.

Expression of an antizyme inhibitor (AZI) in a cell can be achieved according to the invention either by the cell comprising endogenously a homologous nucleic acid which encodes a protein which has the activity of an AZI, or by the cell being transfected with a heterologous nucleic acid by known methods in order to encode a heterologous protein which has the activity of an AZI. It is possible where appropriate for said heterologous protein to be expressed in a cell whose endogenous AZI expression has been inhibited or suppressed in a suitable way, e.g. through deletion of the endogenous AZI gene ("knock-out"), by antisense or cosuppression.

"Effector" means for the purposes of the present invention a molecule able to modulate the activity of the particular target molecule, i.e. of ODC, of AZ or of AZI. The term "effector" may moreover encompass both a purified active ingredient and an unpurified or partially purified substance mixture (e.g. from vegetable or animal extracts) which modulates the function of an ODC, of an AZ or of an AZI, i.e. activates (increases), inhibits (reduces) or affects in a regulatory way the function thereof and thus influences the activity of the ODC, of the AZ or of the AZI, preferably under physiological conditions.

The following examples illustrate the invention without restricting it.

Materials & Methods

Synthetic oligonucleotides were purchased from Metabion (Planegg-Martinsried, Germany) or from MWG-Biotech (Ebersberg, Germany). All other chemicals were from Sigma (Heidelberg, Germany).

Yeasts were transformed by the method of Gietz and Schiestl (Gietz et al., 1995). DNA regions were amplified using specific primers by the method of Saiki et al., (1985).

Further methods for cultivating yeasts are described in, Guide to yeast genetics and molecular biology', Guthrie and Fink, Methods in Enzymology Vol. 194, 1-863,1991. Percentage data are—unless indicated otherwise—percent by weight, % (w/w).

S.cerevisiae Strains

The polyamine-dependent Saccharomyces cerevisiae strain Y15034 (MAT α; his3)1; leu2)0; lys2)0; ura3)0; YKL184w::kanMX4) was purchased from Euroscarf, Frankfurt, Germany. The corresponding wild-type strain Y10000 (MAT α; his3)1; leu2)0; lys2)0; ura3)0) was likewise purchased from Euroscarf. The yeast strains were cultivated either in liquid medium or on a plate at 30° C. The liquid cultures were made up either in YPD pH5.5 (2% glucose,.2% Bacto-Peptone,1% Yeast Extract, Difco Laboratories, Detroit, Mich, USA) or in polyamine-free Synthetic Complete Medium (PFSC, 0.67% Bacto-Yeast Nitrogen Base without amino acids, Difco) with the necessary supplements appropriate for growth of the yeast cells.

The polyamine-free SC medium was sterilized by filtration; the polyamine-free plates were solidified appropriately with 2% agarose (Life Technologies, Paisley, Scotland). Putrescine (Sigma) was added before inoculation with the cells in order to revert the polyamine depletion.

Putrescine stock solution [0.1 mg/ml]

DFMO (Bachem, Heidelberg, Germany) was employed in a concentration of 15 mM (100 mM stock solution).

The yeast expression plasmids p413 ADH, p413 GalL, p413 GalS, p426 ADH, p426 Gal1, p426 GPD, p415 ADH, p415 GalL, p415 GPD are described in Mumberg et al., 1995; Mumberg et al., 1994.

References

Chattopadhyay, M. K., Murakami, Y., and Matsufuji, S. (2001). Antizyme regulates the degradation of ornithine decarboxylase in fission yeast Schizosaccharomyces pombe. Study in the spe2 knockout strains. J. Biol. Chem. 276, 21235-21241.

Coleman, C. S. & Pegg, A. E. (1998). Assay of mammalian ornithine decarboxylase activity using [14C]ornithine. Methods Mol. Biol. 79, 41-44.

Feith, D. J., Shantz, L. M., and Pegg, A. E. (2001). Targeted antizyme expression in the skin of transgenic mice reduces tumor promoter induction of ornithine decarboxylase and decreases sensitivity to chemical carcinogenesis. Cancer Res. 61, 6073-6081.

Gietz, R. D., Schiestl, R. H., Willems, A. R., and Woods, R. A. (1995). Studies on the transformation of intact yeast cells by the LiAc/SS-DNA/PEG procedure. Yeast 11, 355-360.

Iwata, S., Sato, Y., Asada, M., Takagi, M., Tsujimoto, A., Inaba, T., Yamada, T., Sakamoto, S., Yata, J., Shimogori, T., Igarashi, K., and Mizutani, S. (1999). Anti-tumor activity of antizyme which targets the ornithine decarboxylase (ODC) required for cell growth and transformation. Oncogene 18, 165-172.

Janne, J. & Williams-Ashman, H. G. (1971). On the purification of L-ornithine decarboxylase from rat prostate and effects of thiol compounds on the enzyme. J. Biol. Chem. 246,1725-1732.

Johnson, T. D. (1998). Polyamines and cerebral ischemia. Prog. Drug Res. 50, 193-258.

Kawada, M., Someno, T., Inuma, H., Masuda, T., Ishizuka, M., and Takeuchi, T. (2000). The long-lasting antiproliferative effect of 15-deoxyspergualin through its spermidine moiety. J. Antibiot. (Tokyo) 53, 705-710.

Klein, R. D., Favreau, M. A., Alexander-Bowman, S. J., Nulf, S. C., Vanover, L., Winterrowd, C. A., Yarlett, N., Martinez, M., Keithly, J. S., Zantello, M.R., Thomas, E. M., and Geary, T. G. (1997). Haemonchus contortus: cloning and functional expression of a cDNA encoding ornithine decarboxylase and development of a screen for inhibitors. Exp. Parasitol. 87, 171-184.

Mumberg, D., Muller, R., and Funk, M. (1994). Regulatable promoters of Saccharomyces cerevisiae: comparison of transcriptional activity and their use for heterologous expression. Nucleic Acids Res. 22, 5767-5768.

Mumberg, D., Muller, R., and Funk, M. (1995). Yeast vectors for the controlled expression of heterologous proteins in different genetic backgrounds. Gene 156, 119-122.

Saiki, R . K., Scharf, S., Faloona, F., Mullis, K. B., Horn, G. T., Erlich, H. A., and Arnheim, N. (1985). Enzymatic amplification of beta-globin genomic sequences and restriction site analysis for diagnosis of sickle cell anemia. Science 230, 1350-1354.

Seiler, N. (2000). Oxidation of polyamines and brain injury. Neurochem. Res. 25, 471-490.

Seiler, N. & Atanassov, C. L. (1994). The natural polyamines and the immune system. Prog. Drug Res. 43, 87-141.

EXAMPLES

Example 1

Cloning and Sequencing of ODC, and Preparation of ODC Expression Plasmid

The sequence of the ODC gene was amplified from a human liver cDNA library using the following primers:

```
ODC 1.For:                                        (SEQ ID NO: 1)
5'-GGAGAATTCATGAACAACTTTGGTAATGAAGAGTTTGACTGC-3'

ODC 1.Rev:                                        (SEQ ID NO: 2)
5'-TAGCTCGAGCTACACATTAATACTAGCCGAAGCACAGGCTGC-3'
```

The PCR was carried out using Taq polymerase (Life Technologies) in accordance with the manufacturer's statements (30 cycles, 55° C.). The resulting PCR fragment was cloned into the EcoRI-XhoI cleavage sites of the yeast expression vectors p413GalL and p413ADH, and the resulting plasmids were called p413GalL-ODC and p413ADH-ODC.

Example 2

Cloning and Sequencing of Antizymes 1-4 and Preparation of the Antizyme Expression Plasmids In each case two antizyme fragments were generated by combining the primers OAZ.Start/OAZAΔ.Rev and OAZΔ-For/OAZ.Rev, with the antizyme-typical stop codon being deleted from ORF1. These first PCRs were carried out using Pfu polymerase (Stratagene) in accordance with the manufacturer's statements (30 cycles, 53° C.). Using the two resulting antizyme fragments as template, full-length antizyme was prepared in a second PCR together with the primers OAZ.Start and OAZ.Rev. The second PCR was in turn carried out using Pfu polymerase (Stratagene) in accordance with the manufacturer's statements (30 cycles, 53° C.). It was possible to use as OAZ.Start primer for antizyme 4 the same primer as for antizyme 1. Clones from Incyte (Palo Alto, USA) were used as template for amplification of antizyme 3 and antizyme 4.

```
Antizyme 1
OAZ1.Start  5'-GAG GAA TTC ATG GTG AAA TCC TCC GTG CAG CG-3'        (SEQ ID NO: 3)
OAZ1Δ.For   5'-GGT GCT CCT GTG CCC CTC ACC-3'                       (SEQ ID NO: 4)
OAZ1Δ.Rev   5'-GGT GAG GGG CAC AGG AGC AGC-3'                       (SEQ ID NO: 5)
OAZ1.Rev    5'-GCA CTC GAG CTA CTC CTC CTC TCC CGA AGA CTC TCT-3'   (SEQ ID NO: 6)

Antizyme 2
OAZ2.Start  5'-GAG GAA TTC ATG ATA AAC ACC CAG GAC AGT AGT ATT TTG CC-3'  (SEQ ID NO: 7)
OAZ2Δ.For   5'-GTG GTG CTC CGA TGC CCC TCA C-3'                     (SEQ ID NO: 8)
OAZ2Δ.Rev   5'-GTG AGG GGC ATC GGA GCA CCA C-3'                     (SEQ ID NO: 9)
OAZ2.Rev    5'-GCA CTC GAG TTA GTC CTC ATC GGA CAA GTT CTG GTC-3'   (SEQ ID NO: 10)

Antizyme 3
OAZ3.Start  5'-GAG GAA TTC ATG CTG CCT CGT TGT TAT AAA AGC ATC-3'   (SEQ ID NO: 11)
OAZ3Δ.For   5'-TCC AGT GCT CTG AGT CCC TAG-3'                       (SEQ ID NO: 12)
```

```
                                                    -continued
OAZ3Δ.Rev   5'-CTA GGG ACT CAG AGC ACT GGA-3'                         (SEQ ID NO: 13)
OAZ3.Rev    5'-GCA CTC GAG TCA AGG AGG CTC ACT GGG CAG G-3'           (SEQ ID NO: 14)

Antizyme 4
OAZ4.Start  5'-GAG GAA TTC ATG GTG AAA TCC TCC CTG GAG CG-3'          (SEQ ID NO: 3)
OAZ4Δ.For   5'-CGG TGG TGC TCT GAT GTC CCT-3'                         (SEQ ID NO: 15)
OAZ4Δ.Rev   5'-AGG GAC ATC AGA GCA CCA CCG-3'                         (SEQ ID NO: 16)
OAZ4.Rev    5'-GCA CTC GAG CTA GCC CTG CAG CGA GTA GG-3'              (SEQ ID NO: 17)
```

The resulting PCR fragments were cloned into the EcoRI-XhoI cleavage sites of the yeast expression vectors p426ADH, p426Gal1 and p426GPD, and the resulting plasmids were called correspondingly p426ADH-AZ1, p426Gal1-AZ1, p426GPD-AZ1, p426ADH-AZ2, p426Gal1-AZ2, p426GPD-AZ2, p426ADH-AZ3, p426Gal1-AZ3, p426GPD-AZ3, p426ADH-AZ4, p426Gal1-AZ4, p426GPD-AZ4.

Example 3

Cloning and Sequencing of the Antizyme Inhibitor, and Preparation of the Antizyme Inhibitor Expression Plasmid An antizyme inhibitor full-length clone was amplified by PCR from a human liver cDNA library. The following primers were employed for this purpose, using Pfu polymerase (Stratagene) in accordance with the manufacturer's statements (30 cycles, 55° C.).

```
OAISpe1.For                                 (SEQ ID NO: 18)
5'-GGA ACT AGT ATG AAA GGA TTT ATT GAT GAT GCA AAC
TAC TCC G-3'

OAI448.Rev                                  (SEQ ID NO: 19)
5'-TAG CTC GAG TTA AGC TTC AGC GGA AAA GCT GTC TTC
TTG GC-3'
```

The resulting PCR fragment was digested with SpeI/XhoI and cloned into the yeast expression vectors p415ADH, p415GalL and p415GPD. The plasmids were accordingly called p415ADH-AZI, p415GalL-AZI and p415GPD-AZI.

Example 4

ODC Assay

The polyamine-dependent Saccharomyces cerevisiae strain Y15034 and the corresponding wild-type strain Y10000 were each transformed by the Li acetate method with the plasmids p413GalL, p413ADH, p413GalL-ODC and p413ADH-ODC, and the respective transformants were plated out onto Synthetic Complete (SC) Medium (His-, 2% glucose). For each transformation, an overnight culture was inoculated in polyamine-free SC (PFSC) medium (His-, 2% glucose). This was used firstly to carry out a spot test, i.e. the yeasts were adjusted to $OD_{600}$ 3.0 and subjected to 10-fold dilutions (5×). 2 μl of each dilution, starting with $OD_{600}$ 3.0, were placed as a drop on a PFSC plate (His-, 2% galactose/raffinose [1:1]), and the plates were incubated at 30° C. To demonstrate that the growth inhibition is attributable to putrescine depletion, a control was carried out in the presence of putrescine (10 μM).

Secondly, the assay was carried out in liquid medium. Starting from the overnight cultures, the yeasts were started in PFSC medium (His-, 2% galactose/raffinose [1:1]) with an $OD_{600}$ of 0.1, and measurements were taken every hour.

Example 5

Assay for Effectors of ODC Activity

DFMO (difluoromethylornithine) was employed as positive control of an ODC inhibitor. Yeast cells complemented with human ODC (Y15034, p413GalL-ODC), and the corresponding wild-type yeast strain (Y10000) were inoculated overnight. The next day, the growth plots of the yeasts were determined starting from an $OD_{600}$ of 0.05 in the following media:
1. polyamine-free SC medium (His-, 2% galactose/raffinose [1:1])
2. PFSC+DFMO (15 mM)
3. PFSC+DFMO (15 mM)+putrescine (10 μM)

Example 6

Antizyme Assay

The polyamine-dependent yeast strain Y15034 (ODC-knockout) and the corresponding wild-type strain Y10000 were each transformed by the Li acetate method with the plasmid p413GalL-ODC. In addition, each of the 12 antizyme expression plasmids described in Example 2 and, as control, corresponding blank plasmids were cotransformed.

The transformants were plated out on Synthetic Complete (SC) medium (His-, Ura-, 2% glucose, Difco). For each transformation, an overnight culture was inoculated in PFSC medium (His-, Ura-, 2% glucose). This was used firstly to carry out a spot test, i.e. the yeasts were adjusted to $OD_{600}$ 3.0 and subjected to 10-fold dilutions (5×). 2 μl of each dilution, starting with $OD_{600}$ 3.0, were placed as a drop on a PFSC plate (His-, Ura-, 2% galactose/raffinose [1:1]), and the plates were incubated at 30° C.

Expression of the four antizymes 1-4 from the yeast promoters ADH, Gal1 and GPD varied in strength. Antizyme 1 and antizyme 4 achieved inhibition of ODC activity only with the strong GPD promoter (in p426GPD), whereas effective inhibition of ODC activity was made possible also by the ADH promoter for antizyme 2 and also by the Gal1 promoter for antizyme 3. It was possible again to abolish the growth inhibition by addition of putrescine. This shows that the antizyme-related growth inhibition of the yeast cells derives from a polyamine deficiency.

Example 7

Antizyme Inhibitor Assay

The yeasts prepared in Example 6 were each additionally cotransformed with the 3 AZI expression plasmids (p415ADH-AZI, p415GalL-AZI and p415GPD-AZI) described in Example 3 and with the corresponding blank plasmids.

The transformants were plated out on Synthetic Complete (SC) medium (His-, Ura-, Leu-, 2% glucose). For each transformation, an overnight culture was inoculated in PFSC medium (His-, Ura-, Leu-, 2% glucose). This was used firstly to carry out a spot test, i.e. the yeasts were adjusted to $OD_{600}$ 3.0 and subjected to 10-fold dilutions (5×). 2 µl of each dilution, starting with an $OD_{600}$ 3.0 were placed as a drop on a PFSC plate (His-, Ura-, Leu-, 2% galactose/raffinose [1:1]), and the plates were incubated at 30° C.

All promoters were capable of making adequate expression of the antizyme inhibitor possible, so that the ODC inhibition caused by antizyme was abolished.

The invention claimed is:

1. A method for determining the activity of human ornithine decarboxylase, in which yeast cells which express:
   a) human ornithine decarboxylase (ODC),
   b) human antizyme (AZ) and,
   c) human antizyme inhibitor (AZI),
   are cultivated on a polyamine-free medium in the presence and absence of putrescine, and the growth of said cells is determined and positively correlated with said human ODO activity, wherein the endogenous yeast ODO expression in said cells has been inhibited or suppressed during said cultivation.

2. A method for determining the activity of human antizyme, in which yeast cells which express:
   a) human ornithine decarboxylase (ODC),
   b) human antizyme (AZ) and,
   c) human antizyme inhibitor (AZI),
   are cultivated on a polyamine-free medium in the presence and absence of putrescine, wherein the growth of said cells is determined and positively correlated with said human AZ activity, wherein the endogenous yeast AZ expression in said cells has been inhibited or suppressed during said cultivation.

3. A method for determining human antizyme inhibitor activity, in which yeast cells express:
   a) human ornithine decarboxylase (ODC),
   b) human antizyme (AZ) and,
   c) human antizyme inhibitor (AZI),
   are cultivated on a polyamine-free medium in the presence and absence of putrescine, wherein the growth of said calls is determined and positively correlated with said human AZI activity, wherein the endogenous yeast AZI expression in said yeast cells has been inhibited or suppressed during said cultivation.

4. A method for identifying effectors of human ornithine decarboxylase, in which yeast cells express:
   a) human ornithine decarboxylase (ODC),
   b) human antizyme (AZ), and
   c) human antizyme inhibitor (AZI),
   are cultivated in the presence and absence of a test substance to be investigated as an effector of ODC;
   wherein said cultivation is carried out in a polyamine-free medium in the presence and absence of putrescine; and
   the growth of said cells is measured to determine the effect of said test substance on the activity of said human ODC;
   wherein the growth of said cells is determined and positively correlated with said human ODC activity; and
   wherein the endogenous yeast ODC expression in said cells has been inhibited or suppressed during cultivation.

5. A method for identifying effectors of human antizyme, in which yeast cells which express:
   a) human ornithine decarboxylase (ODC),
   b) human antizyme (AZ) and,
   c) human antizyme inhibitor (AZI),
   are cultivated in the presence and absence of a test substance to be investigated as an effector of AZ;
   wherein said cultivation is carried out in a polyamine-free medium in the presence and absence of putrescine; and
   the growth of said cells is measured to determine the effect of said test substance on the activity of said human AZ;
   wherein the growth of said cells is determined and positively correlated with said human AZ activity; and
   wherein the endogenous yeast AZ expression in said cells has been inhibited or suppressed during said cultivation.

6. A method for identifying effectors of human antizyme, in which yeast ceils which express:
   a) human ornithine decarboxylase (ODC),
   b) human antizyme (AZ) and,
   c) human antizyme inhibitor (AZI), are cultivated in the presence and absence of a test substance to be investigated as an effector of AZI;
   wherein said cultivation is carried out in a polyamine-free medium in the presence and absence of putrescine; wherein
   the growth of said cells is measured to determine the effect of said test substance on the activity of said human AZI;
   wherein the growth of said cells is determined and positively correlated with said human AZI activity; and
   wherein the endogenous yeast AZI expression in said cells has been inhibited or suppressed during said cultivation.

* * * * *

SEQUENCE LISTING

```
<160> NUMBER OF SEQ ID NOS: 19

<210> SEQ ID NO 1
<211> LENGTH: 42
<212> TYPE: DNA
<213> ORGANISM: Artificial Sequence
<220> FEATURE:
<223> OTHER INFORMATION: PCR Primer

<400> SEQUENCE: 1
ggagaattca tgaacaactt tggtaatgaa gagtttgact gc                          42

<210> SEQ ID NO 2
<211> LENGTH: 42
<212> TYPE: DNA
<213> ORGANISM: Artificial Sequence
<220> FEATURE:
<223> OTHER INFORMATION: PCR Primer

<400> SEQUENCE: 2
tagctcgagc tacacattaa tactagccga agcacaggct gc                          42

<210> SEQ ID NO 3
<211> LENGTH: 32
<212> TYPE: DNA
<213> ORGANISM: Artificial Sequence
<220> FEATURE:
<223> OTHER INFORMATION: PCR Primer

<400> SEQUENCE: 3
gaggaattca tggtgaaatc ctccctgcag cg                                     32

<210> SEQ ID NO 4
<211> LENGTH: 21
<212> TYPE: DNA
<213> ORGANISM: Artificial Sequence
<220> FEATURE:
<223> OTHER INFORMATION: PCR Primer

<400> SEQUENCE: 4
ggtgctcctg tgccctcac c                                                 21

<210> SEQ ID NO 5
<211> LENGTH: 21
<212> TYPE: DNA
<213> ORGANISM: Artificial Sequence
<220> FEATURE:
<223> OTHER INFORMATION: PCR Primer

<400> SEQUENCE: 5 ggtgagggc acaggagcac c                                                 21

<210> SEQ ID NO 6
<211> LENGTH: 40
<212> TYPE: DNA
<213> ORGANISM: Artificial Sequence
<220> FEATURE:
<223> OTHER INFORMATION: PCR Primer
```

<400> SEQUENCE: 6
gcactcgagc tactcctcct cctctcccga agactctctc                          40

<210> SEQ ID NO 7
<211> LENGTH: 41
<212> TYPE: DNA
<213> ORGANISM: Artificial Sequence
<220> FEATURE:
<223> OTHER INFORMATION: PCR Primer

<400> SEQUENCE: 7
gaggaattca tgataaacac ccaggacagt agtattttgc c                        41

<210> SEQ ID NO 8
<211> LENGTH: 22
<212> TYPE: DNA
<213> ORGANISM: Artificial Sequence
<220> FEATURE:
<223> OTHER INFORMATION: PCR Primer

<400> SEQUENCE: 8
gtggtgctcc gatgcccctc ac                                             22

<210> SEQ ID NO 9
<211> LENGTH: 22
<212> TYPE: DNA
<213> ORGANISM: Artificial Sequence
<220> FEATURE:
<223> OTHER INFORMATION: PCR Primer

<400> SEQUENCE: 9
gtgaggggca tcggagcacc ac                                             22

<210> SEQ ID NO 10
<211> LENGTH: 36
<212> TYPE: DNA
<213> ORGANISM: Artificial Sequence
<220> FEATURE:
<223> OTHER INFORMATION: PCR Primer

<400> SEQUENCE: 10
gcactcgagt tagtcctcat cggacaagtt ctggtc                              36

<210> SEQ ID NO 11
<211> LENGTH: 36
<212> TYPE: DNA
<213> ORGANISM: Artificial Sequence
<220> FEATURE:
<223> OTHER INFORMATION: PCR Primer

<400> SEQUENCE: 11
gaggaattca tgctgcctcg ttgttataaa agcatc                              36

<210> SEQ ID NO 12
<211> LENGTH: 21
<212> TYPE: DNA
<213> ORGANISM: Artificial Sequence
<220> FEATURE:
<223> OTHER INFORMATION: PCR Primer

<400> SEQUENCE: 12
tccagtgctc tgagtcccta g                                              21

<210> SEQ ID NO 13
<211> LENGTH: 21

<212> TYPE: DNA
<213> ORGANISM: Artificial Sequence
<220> FEATURE:
<223> OTHER INFORMATION: PCR Primer

<400> SEQUENCE: 13
ctagggactc agagcactgg a                                       21

<210> SEQ ID NO 14
<211> LENGTH: 31
<212> TYPE: DNA
<213> ORGANISM: Artificial Sequence
<220> FEATURE:
<223> OTHER INFORMATION: PCR Primer

<400> SEQUENCE: 14
gcactcgagt caaggaggct cactgggcag g                            31

<210> SEQ ID NO 15
<211> LENGTH: 21
<212> TYPE: DNA
<213> ORGANISM: Artificial Sequence
<220> FEATURE:
<223> OTHER INFORMATION: PCR Primer

<400> SEQUENCE: 15
cggtggtgct ctgatgtccc t                                       21

<210> SEQ ID NO 16
<211> LENGTH: 21
<212> TYPE: DNA
<213> ORGANISM: Artificial Sequence
<220> FEATURE:
<223> OTHER INFORMATION: PCR Primer

<400> SEQUENCE: 16
agggacatca gagcaccacc g                                       21

<210> SEQ ID NO 17
<211> LENGTH: 29
<212> TYPE: DNA
<213> ORGANISM: Artificial Sequence
<220> FEATURE:
<223> OTHER INFORMATION: PCR Primer

<400> SEQUENCE: 17
gcactcgagc tagccctgca gcgagtagg                               29

<210> SEQ ID NO 18
<211> LENGTH: 43
<212> TYPE: DNA
<213> ORGANISM: Artificial Sequence
<220> FEATURE:
<223> OTHER INFORMATION: PCR Primer

<400> SEQUENCE: 18
ggaactagta tgaaaggatt tattgatgat gcaaactact ccg               43

<210> SEQ ID NO 19
<211> LENGTH: 41
<212> TYPE: DNA
<213> ORGANISM: Artificial Sequence
<220> FEATURE:
<223> OTHER INFORMATION: PCR Primer -continued

```
<400> SEQUENCE: 19
tagctcgagt taagcttcag cggaaaagct gtcttcttgg c          41
```